United States Patent [19]

Sulc et al.

[11] Patent Number: 4,994,083
[45] Date of Patent: Feb. 19, 1991

[54] SOFT INTRACAMERAL LENS

[75] Inventors: Jiří Sulc; Zuzana Krcová; Karel Smetana; Šárka Pitrová, all of Prague, Czechoslovakia

[73] Assignee: Ceskoslovenska akademie ved, Prague, Czechoslovakia

[21] Appl. No.: 527,653

[22] Filed: May 21, 1990

Related U.S. Application Data

[62] Division of Ser. No. 379,575, Jul. 13, 1989, Pat. No. 4,955,903, which is a division of Ser. No. 76,127, Jul. 21, 1987.

[30] Foreign Application Priority Data

Jul. 22, 1986 [CS] Czechoslovakia ............... 5559-86

[51] Int. Cl.$^5$ ............................................. A61F 2/16
[52] U.S. Cl. ............................................. 623/6
[58] Field of Search .................... 623/6; 351/160 H

[56] References Cited

U.S. PATENT DOCUMENTS

| 3,866,249 | 2/1975 | Flom | 623/6 |
| 4,664,666 | 5/1987 | Barrett | 623/6 |
| 4,713,244 | 12/1987 | Bawa et al. | 351/160 H X |

FOREIGN PATENT DOCUMENTS

| 2151371A | 7/1985 | United Kingdom | 623/6 |

*Primary Examiner*—Alan W. Cannon
*Attorney, Agent, or Firm*—Leydig, Voit & Mayer

[57] ABSTRACT

The invention pertains to a soft intracameral lens determined for the location in the posterior chamber of eye.

The soft intracameral hydrogel lens has its front supporting and centering convex part determined for leaning against iris having in front a rotation symmetrical shape of a sphere, paraboloid or hyperboloid and passing into the broadest circumference by a surface which shape is equal to or approaches a shape of lateral area of cone, while the hinder supporting part of the lens with a spherical, planar, or moderately convex or concave-curved shape for leaning against a hinder capsula or a membrane from vitreous body in a large surface area. The hinder supporting part is broadened and forms on the edge a retaining ring reaching over the front part as much as by 1.5 mm, whereas the central thickness of the lens ranges between 1 to 3.5 mm. The surface of the soft intracameral lens may be formed, at least in part, from a soft hydrogel containing at least 70% of water at 20° C. in the state of equilibrium swelling. the lens may have a spherical shape and be provided on the circumference with a supporting collar from soft hydrogel. The lens may also contain inside in its optical axis an inner part, e.g. a Fresnel lens, with a higher refractive index of light than has the surrounding part of the lens.

3 Claims, 1 Drawing Sheet

SOFT INTRACAMERAL LENS

This is a division of application Ser. No. 379,575, filed July 13, 1989 now U.S. Pat. No. 4,955,903; which is a division of Ser. No. 076,127, filed July 21, 1987, pending.

The invention pertains to a soft intracameral lens.

Common optical defects of eye are usually corrected either with additional lenses placed in front of the eye (spectacles, monocle) or on the eye surface (contact lenses) or with lenses replacing the original lens of the eye. These substitute lenses had so far the form of very thick converging spectacle lenses, however the development now points to intracameral lenses placed directly in the eye from which the natural lens had been removed (e.g. in the operation of cataract).

Provided the original capsula (capsula lentis) is retained after operation, even a hard intracameral lens may be placed in it. However, the disadvantage consists in a higher refractive index of the hard lens from organic glass and thus in its smaller dimension than had the original natural lens and, besides, also in its higher specific mass. The last fact makes necessary to fix the substitute lens mechanically precisely in the optical axis of eye, which requires additional fixation means and makes the location in the correct position very difficult.

It would be therefore highly purposeful to develop intracameral lenses from a soft elastic material which would enable the easier introduction into eye in a deformed or dry state and the specific mass of which would approach the specific mass of natural lens.

This is why the experiments were carried out with hydrogels which so far proved suitable for soft contact lenses, above all with a lightly crosslinked poly(2-hydroxyethyl methacrylate) (polyHEMA). However, it turned out that this material is not suitable for the production of intracameral lenses because minute calcifications are created on its surface so that the lens loses its original transparency. From this point of view, the intracameral lenses from highly swelling gels proved better, e.g. from gels with the swelling capacity in water at 20° C. amounting to 55-70%. But the problem of correct centration and permanent location in the eye axis still remains unsolved. In addition, the high content of water in highly swelling gels lowers the refractive index and thus causes an considerable increase of lens thickness.

Intracameral lenses used at the present time are produced in a broad scale of shapes and are located in various parts of eye—in the anterior chamber, pupil, and, most frequently, in the posterior chamber. The major part of these lenses is manufactured from a hard organic glass—poly(methyl methacrylate). Recently are reported soft lenses from silicon rubber and from hydrogels.

All types of these lenses consist of two basic parts—of the optical part and the supporting part. The optical part is formed by a converging lens with value 15-20 Dpt. The supporting part centers the lens and stabilizes its position.

The supporting system made from various materials, for example, poly(methyl methacrylate), polypropylene or polyester, always wounds the parts of eye against which it leans. Since most materials have a considerable specific mass and the surface of support action is very small, undesirable reactions to foreign body often occur at the contact place and cause various complications after introduction of the lenses.

Besides, the hard intracameral lenses have the disadvantage that they require a relatively large incision for introduction into eye because they cannot be elastically deformed. Another disadvantage is their impermeability for gases, liquids, and ions.

The invention solves the above problems by the design of lens which ensues from specific properties of soft types of hydrogels with a high content of water and a low Young modulus combined with the shape adaptability providing the intracameral lens with optical properties of a natural lens. The soft intracameral lens according to the invention determined for the location in the posterior chamber of eye, reaches with its front supporting and centering convex part up to a pupil, in which it is spontaneously centered, while the surface area of this front part continuously passes into a surface equal to or approaching the shape of lateral area of cone and the hinder supporting part of the lens leans against a hinder capsula or a membrane from vitreous body. The hinder part is broadened and forms a retaining (safety) ring exceeding the front centering and supporting part as much as by 1.5 mm. This retaining ring protects the lens from sliding out into the anterior chamber of eye. The central thickness of lens ranges advantageously from 1 mm to 3.5 mm. The shape and size of lens cause its automatic location in the eye axis.

In order to exclude the wounding, very important is the softness of lens surface and therefore the lens according to the invention may be either completely homogeneous from the single kind of material with a single value of refractive index, or from two different materials, namely from a core with a higher refractive index and a casing with a lower refractive index, or it may be from the material which refractive index continuously decreases from the center to the circumference of lens. The desired value can be attained by suitable combination of two materials with different refractive indexes, even if the refractive index of the soft swollen casing is lower than optimum. It is understood that also further properties change with the variation of refractive index, namely Young modulus and hardness of the material. In order to reduce the volume of the inner part of lens, this inner part may have the form of a small Fresnel lens, the concentric or spiral scratches of which and their edges are suitably protected with the hydrogel coating against any kind of damage.

The front side of lens reaching into pupil is automatically centered in the pupil in such a way, that it has a convex rotation symmetrical shape of a sphere or paraboloid or hyperboloid in front and this shape passes to the broadest circumference as a surface with the shape equal to or approaching the shape of lateral area of cone, whereas the hinder side leaning against the vitreous body or the hinder capsula has a spherical or planar shape, or a moderately concave or convex shape, or corresponds to the shape of a lower part of rotation elipsoid. The automatic centering may be alternatively obtained by the combinations of the spherical shape of lens with a collar or without it. All surface parts coming into contact with eye tissues must be made of the material with a high content of water and low modulus.

The lens according to the invention may be thus defined in such a way, that it has the shape causing an automatic centering by its front convex surface leaning against iris or against the edge of pupil which is overlapped with a hinder side resting on the membrane from vitreous body or on the capsula of lens, whereas all surface parts of the lens which are in contact with eye tissues are from a soft hydrogel containing at least 70%, advantageously at least 90%, of water in the equilibrium swollen state at 20° C. The lens may have inside a harder core with a higher refractive index and with the abrupt or continuous transition between both materials. For example, the continuous transition of refractive index can be attained by partial swelling of a lens from polyHEMA with alkaline hydroxide, so that the core remains intacted and swells only with 40% of water (example 1).

An advantage of the lens according to the invention is that the lens does not wound any part of eye and does not need any support, fastening, and centering means. The highly swelling hydrogel remains clean on the surface, lymphocytes or other cells do not deposit on it, and has not tendency to form calcifications. A great advantage is its easy introduction in the partially or completely dried state, i.e. at its small volume. In the state of only partial drying, the gel is flexible and can be easily deformed in order to facilitate the insertion even more. The dry or almost dry lens increases its volume by swelling about tentimes or more and thus fills up the given space and locates itself in the eye axis if the insertion was at least approximately correct. The lens is fixed with the iris on the front side and sits on vitreous body with its hinder side.

A small difference between the specific masses of the lens and chamber liquor can be compensated by including a drop of oil into the lens edge during polymerization.

The lens implanted in this way does not seal the back part of iris even when it sits on iris, since its surface is softer than the surface of iris. This fact also enables the circulation of chamber liquor in the same way as in a sound eye.

Since the lens is supported in front and at the back on a large surface, specific pressures on the neighbouring tissues are substantially reduced and a danger of pressure necroses does not occur.

The lens according to the invention may be inserted into the original capsula of the natural lens, but it can be implanted also without this capsula.

The soft material with a low modulus enables a partial accommodation of eye.

The lenses according to the invention may be produced, for example, by pressing a prefabricate from a non-crosslinked copolymer of 2-hydroxyethyl methacrylate with a small amount of ethylene dimethacrylate in a mold in the presence of a strongly acid catalyst. (Ethylene dimethacrylate, which usually acts as a crosslinking agent, gives in the procedure according to Czechoslovak Pat. No. 141,101—Chromecek et al., a copolymer well soluble e.g. in methanol, which is at utmost branched but not crosslinked). Other method of manufacturing is the common casting of a mixture of 2-hydroxyethyl methacrylate with less than 2% of ethylene dimethacrylate containing less than 39% of water in stable or rotating molds and the following reorganization of covalent network by heating with alkaline hydroxide. Further possible procedure is described in the U.S. patent application No. 022,074 and consists in the crosslinking polymerization of a drop of HEMA containing less than 1% of a crosslinking agent in a mold filled with a liquid immiscible with the given monomers under simultaneous pressing of the polymerizing mixture into the final shape.

The reorganization of covalent network with the simultaneous increase of the swelling capacity of polymer in water may be carried out also only in the surface layer of lens in such a way, that the action of the above given reagents (an acid catalyst or alkaline hydroxide) is limited and the reagent does not penetrate into the whole mass of lens.

The invention is further illustrated in examples of performance and in drawings showing in FIG. 1–4 diagrammatically various shapes of the intracameral lenses according to the invention in partional sectional view.

FIG. 1 shows the lens which has the front paraboloidal supporting and centering convex part 1 determined for leaning against iris and a moderately convex hinder supporting part 2 enabling leaning of the lens against the back capsula or a membrane of vitreous body on a large surface area. The hinder supporting part 2 is broadened and forms the retaining ring 3 on the lens edge, which secures the lens against sliding out into the anterior chamber of eye.

The lens drawn in FIG. 2 has, in contradistinction to the lens in FIG. 1, the front supporting and centering convex part 1 of spherical shape which passes into the shape of the lateral area of cone.

EXAMPLE 1

Figure 1:
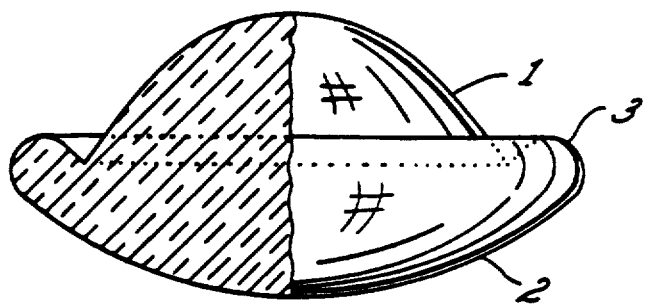
Figure 2:
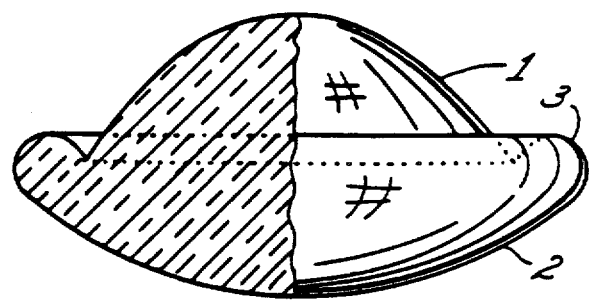
Figure 3:
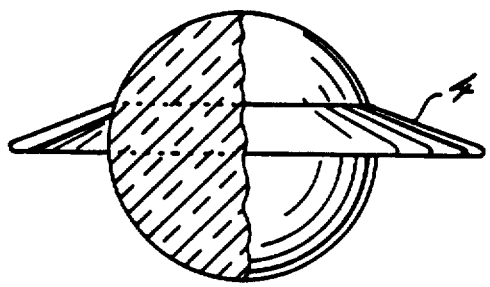
FIG. 3 shows the lens of spherical shape provided on the edge with a soft hydrogel collar 4, which acts as the retaining ring 3 in FIG. 1.
Figure 4:
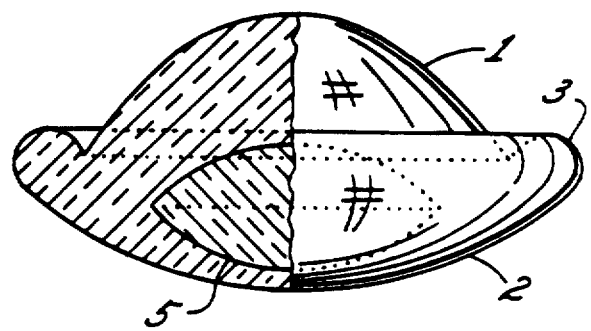
FIG. 4 shows the lens according to FIG. 1, which accommodates inside in the optical axis the inner part 5 having a higher refractive index of light than has the neighbouring hydrogel surrounding this part from all sides.

A lens with the shape shown in FIG. 1 was cast in an adequately scaled-down mold with the addition of 0.3% of isopropyl peroxocarbonate in the presence of 20% of water in monomer mixture. After completion of the polymerization, the lens was washed with distilled water and immersed into 30% sodium hydroxide for 1 hour, the hydroxide was removed from the surface with a filter paper, and the lens was heated in an atmosphere saturated with steam by infrared radiation above 40° C. for 16 hours, washed with distilled water, and stored in a 0.8% solution of sodium chloride. The prepared lens increased the volume by about 40% in comparison with the original casting and was strongly swollen in the surface layer, which contained about 93% of water. In the inwards direction, the swelling capacity of the lens continuously decreased. The overall swelling capacity was 88.5% of water at 20° C. in the state of equilibrium swelling.

EXAMPLE 2

The procedure according to example 1 was repeated with the distinction that the mold was even somewhat smaller and the lens was, after washing with water, allowed in the 30% sodium hydroxide for 24 hours at 2° C. and then transferred together with a vessel and hydroxide into a thermostated bath, where it was heated to 35° C. for another 24 hours. The lens was then thoroughly washed and had the swelling capacity 81% of water at 20° C. The swelling in physiologic saline at pH 7.1 was 63%. It was easily applicable after partial drying and reduction of volume and did not required centering and fixation after reswelling in eye.

EXAMPLE 3

The required amount of refined paraffin oil and a drop of monomer mixture consisting of 2-hydroxyethyl methacrylate with 0.3% of ethylene glycol dimethacrylate, 35% of water, and 0.1% of azo-bis-isobutyronitrile were introduced into a polypropylene mold with spherical surface and the mold was closed with a shaped polypropylene punch and heated to 60° C. for 4 hours in nitrogen atmosphere. The punch was provided on the edge with cuttings enabling the oil to overflow while the edge of the punch did not tightly fit to the mold. The uverrun monomer mixture created a rounded border. The mold was then opened and the lens spontaneously fell out. It was rinsed with petroleum, allowed to dry, immersed into a 120° C. warm mixture from 1 part of sulfuric acid and 3 parts of anhydrous glycerol for 2 minutes, and thoroughly washed with water. It was eventually stored in physiologic saline. The lens had a very soft surface layer with such a low friction coefficient that it very facilitated an automatic centering of the lens in the posterior chember of eye.

EXAMPLE 4

A small Fresnel lens with fine scratches was polymerized into a viscous polymerizing mixture of 2-hydroxyethyl methacrylate with methacrylic acid giving a copolymer swelling, after washing and neutralization to pH 7.1, to the water content of 90%. The polymerization was carried out using sodium persulfate and such a slow heating of the mixture which enabled to locate the small Fresnel lens from poly(butyl methacrylate) in the center of a transparent mold at a considerable viscosity of the polymerizing mixture but still before the gelation point, which was then rapidly achieved by heating with a source of infrared radiation before the Fresnel lens could change its position. The upper side of mold was free but surrounded with an atmosphere of pure nitrogen.

The invention is not limited to the present examples which only illustrate the various possible methods of preparation being not the object of this invention as such.

We claim:

1. A soft intracameral lens adapted for location in the posterior chamber of an eye having an outer part which surrounds an inner part, said lens comprising a convex front supporting and centering part which, after location of the lens in the posterior chamber of the eye, protrudes anteriorally to the posterior chamber and contacts the iris such that said lens is centered in the eye, the surface of said front part being selected from the group consisting of spheroidal, paraboloidal and hyperboloidal surfaces, a rear supporting part which, after the location of said lens in the posterior chamber of the eye, is adapted for contacting a capsula or a membrane of the eye, the surface of said rear part being selected from the group consisting of spheroidal, paraboloidal and hyperboloidal surfaces, and a retaining ring located on said rear supporting part comprising an anterior surface, said anterior surface extending radially outward from said rear supporting part, wherein the outward extension of the anterior surface of said ring ranges from about 1 mm to about 3.5 mm, said lens after location in the posterior chamber of the eye being self-centering and self-supporting without the need for additional supporting or centering means, and all surface parts of the lens which contact eye tissue being formed from a soft hydrogel which will not wound the eye tissues, wherein the inner part of the lens is located such that the optical axis of the lens passes through said inner part, said inner part possessing a higher refractive index of light than the outer part.

2. The soft hydrogel intracameral lens according to claim 1, wherein the refractive index of light changes throughout the inner and outer parts, said index being equal at the interface of said inner and outer parts.

3. The soft hydrogel intracameral lens according to claim 1, wherein the inner part has the form of a Fresnel lens.

* * * * *